US00PP25148P2

(12) United States Plant Patent
Fortune

(10) Patent No.: US PP25,148 P2
(45) Date of Patent: Dec. 2, 2014

(54) DIANELLA PLANT NAMED 'FORTUNEGOLD'

(50) Latin Name: ***Dianella* hybrid**
Varietal Denomination: Fortunegold

(71) Applicant: Mieke Fortune, North Arm (AU)

(72) Inventor: Mieke Fortune, North Arm (AU)

(73) Assignee: Mieke & Graham Fortune, North Arm, Queensland (AU), as Trustees for Mega Fortune Super Fund ( * ) Notice: Subject to any disclaimer, the term of this patent is extended or adjusted under 35 U.S.C. 154(b) by 0 days.

(21) Appl. No.: 13/987,347

(22) Filed: Jul. 15, 2013

(51) Int. Cl.
*A01H 5/00* (2006.01)

(52) U.S. Cl.
USPC ..... Plt./424

(58) Field of Classification Search
CPC ..... A01H 5/00
USPC ..... Plt./424
See application file for complete search history.

(56) References Cited

PUBLICATIONS

UPOV hit for 'Fortunegold', Pluto Plant Variety Database, AU PBR 201355, application date Jul. 5, 2013.*

* cited by examiner

*Primary Examiner* — Anne Grunberg
(74) *Attorney, Agent, or Firm* — C. A. Whealy

(57) ABSTRACT

A new and distinct cultivar of *Dianella* plant named 'Fortunegold', characterized by its upright and outwardly arching plant habit; vigorous growth habit; medium plant size; broad and glossy yellow green, grey green and yellow variegated leaves arranged in basal rosettes; violet blue-colored flowers; and good garden performance.

4 Drawing Sheets

Botanical designation: *Dianella* hybrid.
Cultivar denomination: 'FORTUNEGOLD'.

BACKGROUND OF THE INVENTION

The present invention relates to a new and distinct cultivar of *Dianella* plant, botanically known as *Dianella* hybrid, commonly referred to Blue Flax Lily, typically used as an ornamental landscape plant and hereinafter referred to by the name 'Fortunegold'.

The new *Dianella* plant is a naturally-occurring single shoot mutation of an unnamed selection of *Dianella* hybrid, not patented. The new *Dianella* plant was discovered and selected by the Inventor on a single plant from within a population of plants of the unnamed selection in a controlled nursery environment in Yandina, Queensland, Australia in 2007.

Asexual reproduction of the new *Dianella* plant by divisions in Yandina, Queensland, Australia since 2007 has shown that the unique features of this new *Dianella* plant are stable and reproduced true to type in successive generations.

SUMMARY OF THE INVENTION

Plants of the new *Dianella* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Fortunegold'. These characteristics in combination distinguish 'Fortunegold' as a new and distinct *Dianella* plant:

1. Upright and outwardly arching plant habit.
2. Vigorous growth habit; medium plant size.
3. Broad and glossy yellow green, grey green and yellow variegated leaves arranged in basal rosettes.
4. Violet blue-colored flowers.
5. Good garden performance.

Plants of the new *Dianella* differ from plants of the mutation parent selection in leaf color as plants of the mutation parent selection have non-variegated green-colored leaves.

Plants of the new *Dianella* can be compared to plants of *Dianella* hybrid 'Variegata', not patented. In side-by-side comparisons conducted in Yandina, Queensland, Australia, plants of the new *Dianella* differed primarily from plants of 'Variegata' in leaf color as plants of 'Variegata' had yellow green and white variegated leaves.

Plants of the new *Dianella* can also be compared to plants of *Dianella* hybrid 'Sougold', disclosed in U.S. Plant Pat. No. 13,705. In side-by-side comparisons conducted in Yandina, Queensland, Australia, plants of the new *Dianella* differed primarily from plants of 'Sougold' in the following characteristics:

1. Plants of the new *Dianella* were shorter than plants of 'Sougold'.
2. Plants of the new *Dianella* and 'Sougold' differed in leaf coloration.
3. Plants of the new *Dianella* had inflorescences that were taller in relationship to the foliar plane than plants of 'Sougold'.
4. Plants of the new *Dianella* and 'Sougold' differed in flower coloration.

BRIEF DESCRIPTION OF THE PHOTOGRAPHS

The accompanying photographs illustrate the overall appearance of the new *Dianella* plant showing the colors as true as it is reasonably possible to obtain in colored reproductions of this type. Colors in the photographs may differ slightly from the color values cited in the detailed botanical description which accurately describe the colors ofthe new *Dianella* plant.

The photograph on the first sheet comprises a side perspective view of a typical plant of 'Fortunegold' grown in a container.

The photograph on the second sheet comprises a top perspective view of a typical plant of 'Fortunegold' grown in a container.

The photograph on the third sheet comprises a close-up view of typical leaves of 'Fortunegold'.

The photograph on the fourth sheet comprises a close up view of a typical flowering plant of 'Fortunegold'.

DETAILED BOTANICAL DESCRIPTION

The aforementioned photographs and following observations and measurements describe plants grown during the autumn and winter in 95-cm (550-ml) containers in a polyethylene-covered shadehouse in Yandina, Queensland, Australia and under cultural practices typical of commercial *Dianella* plant production. During the production of the plants, day temperatures ranged from 2° C. to 36° C., night temperatures ranged from 2° C. to 27° C. and light levels averaged 33 klux. Vegetative plants were six months old when the photographs and description were taken. Flowering plants were two years old when the photographs and description were taken. For the In the following description, color references are made to The Royal Horticultural Society Colour Chart, 2007 Edition, except where general terms of ordinary dictionary significance are used.

Botanical classification: *Dianella* hybrid 'Fortunegold'.

Parentage: Naturally-occurring branch mutation of an unnamed selection of *Dianella* hybrid, not patented.

Propagation:

*Type*.—By tissue culture.

*Time to initiate roots, summer*.—About ten days at temperatures about 23° to 25° C.

*Time to initiate roots, winter*.—About 20 days at temperatures about 23° to 25° C.

*Time to produce a rooted plant, summer*.—About 12 to 16 weeks at temperatures about 25° C.

*Time to produce a rooted plant, winter*.—About 20 to 24 weeks at temperatures about 15° C.

*Root description*.—Medium in thickness, fleshy; white in color.

*Rooting habit*.—Moderately freely branching; medium density.

Plant description:

*Plant and growth habit*.—Semi-compact, upright and outwardly arching plant habit; canes absent; medium dense to dense growth habit.

*Plant height, soil level to top of foliar plane*.—About 40 cm to 50 cm.

*Plant height, soil level to top of inflorescences*.—About 40 cm to 60 cm.

*Plant diameter or spread*.—About 40 cm to 50 cm.

Leaf description:

*Appearance*.—Leaves erect to sem-erect; from the middle of the leaf to the apex, arching to weeping; leaves two-ranked and simple; grass-like; sheathing; arranged in a upright basal rosette.

*Length*.—About 50 cm to 60 cm.

*Width*.—About 2.4 cm to 2.8 cm.

*Shape*.—Ligulate.

*Apex*.—Acute.

*Base*.—Sheathing.

*Margin*.—Serrulate.

*Cross-section*.—Concave to almost flat towards the apex.

*Texture, upper and lower surfaces*.—Smooth, glabrous; glaucous; lower surface with fine spines along the midrib.

*Luster, upper surface*.—Glossy.

*Luster, lower surface*.—Medium glossiness.

*Venation pattern*.—Parallel.

*Color*.—Developing leaves, upper and lower surfaces: Close to 144C to 144D becoming closer to 144A with development. Fully expanded leaves, upper surface: Conspicuous variegation patterning of longitudinal stripes parallel with venation present along the entire leaf length with color bands of variable width and close to N137A, N137C, 191A, 3B and 4B in color. Fully expanded leaves, lower surface: Conspicuous variegation patterning of longitudinal stripes parallel with venation present along the entire leaf length with color bands of variable width and close to N137A, 4B and 5C in color. Venation, upper and lower surfaces: Similar to leaf surface coloration. Basal sheath: Close to NN155B and 144C to 144D.

Inflorescence description:

*Inflorescence type and form*.—Inflorescences are loosely-branching upright panicles; freely flowering habit with about 70 to 100 flowers developing per inflorescence; flowers withering and not persistent.

*Inflorescence length*.—About 40 cm to 60 cm.

*Inflorescence width*.—About 15 cm to 20 cm.

*Flowers*.—Diameter: About 4 mm to 5 mm. Tepal appearance: Six tepals that are straight to slightly spreading and fused at the base. Tepal length: About 5 mm to 7 mm. Tepal width: About 2 mm to 3 mm. Tepal shape: Elliptic. Tepal apex: Acute. Tepal margin: Entire. Tepal color, upper surface: Close to N89A; towards the apex, close to 90A. Tepal color, lower surface: Close to N89A; towards the apex, close to 90A.

*Flower buds*.—Height: About 6 mm to 10 mm. Diameter: About 2 mm to 3 mm. Shape: Elliptic. Color: Close to N89A.

*Peduncles*.—Length: About 40 cm to 60 cm. Texture: Smooth, glabrous. Strength: Strong, flexible. Color: Close to between 144A and 146C.

*Pedicels*.—Length: About 5 mm to 8 mm. Texture: Smooth, glabrous. Strength: Strong, flexible. Color: Close to 146A to 146B.

*Reproductive organs*.—Stamens: Quantity per flower: Typically six. Stamen length: About 6 mm to 9 mm. Filament color: Close to 94B to 94C. Anther shape: Narrowly oblong. Anther color: Close to 23A. Pollen amount: None observed. Pistils: Quantity per flower: Typically one. Pistil length: About 6 mm to 9 mm. Stigma color: Close to 91D.

*Seeds and fruits*.—Seed and fruit production has not been observed on plants of the new *Dianella*.

Disease & pest resistance: Plants of the new *Dianella* have been shown to be resistant to root rot. Plants of the new *Dianella* have not been shown to be resistant to pests and other pathogens common to *Dianella* plants.

Garden performance: Plants of the new *Dianella* have been observed to have good garden performance and tolerate shade, wind, rain, drought and temperatures ranging from about 0° C. to about 42° C.

It is claimed:

1. A new and distinct *Dianella* plant named 'Fortunegold' as illustrated and described.

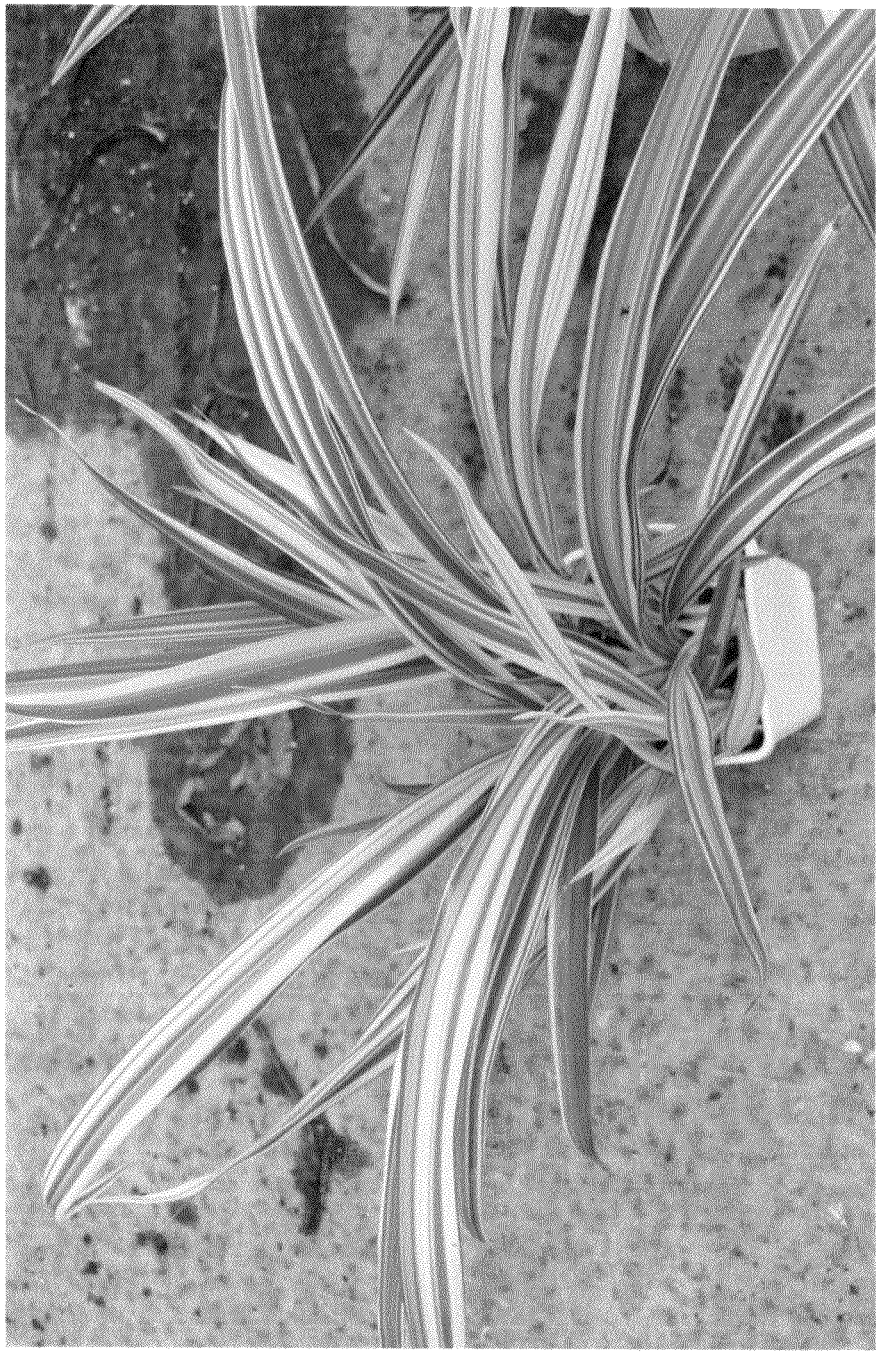

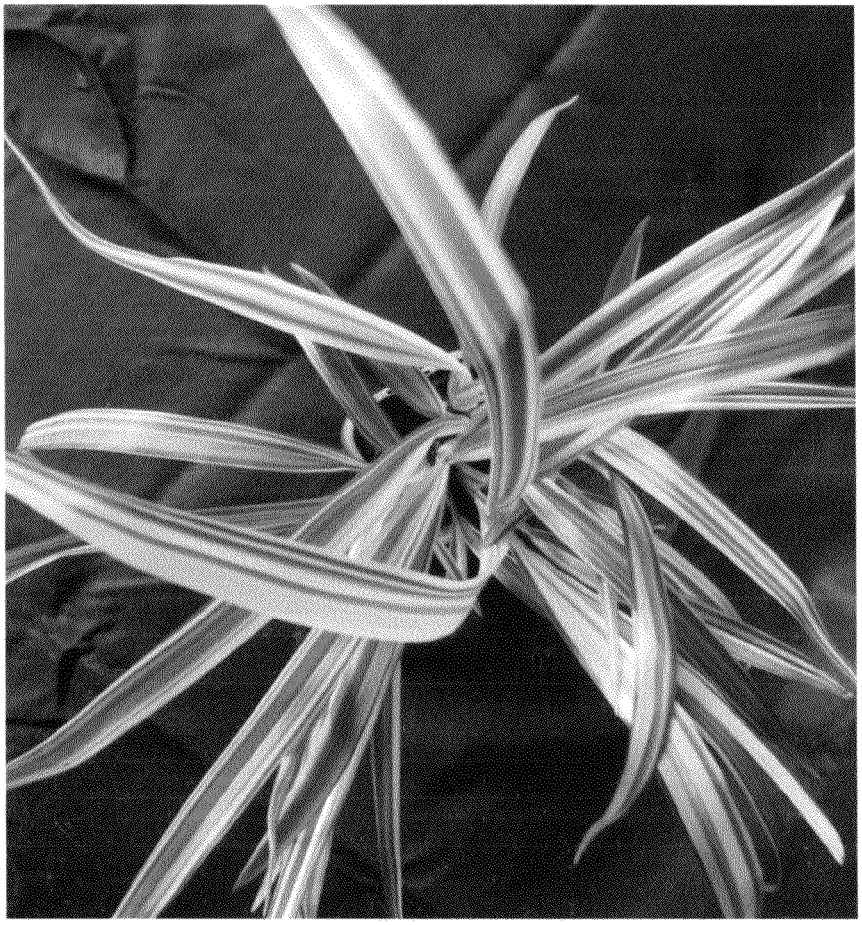

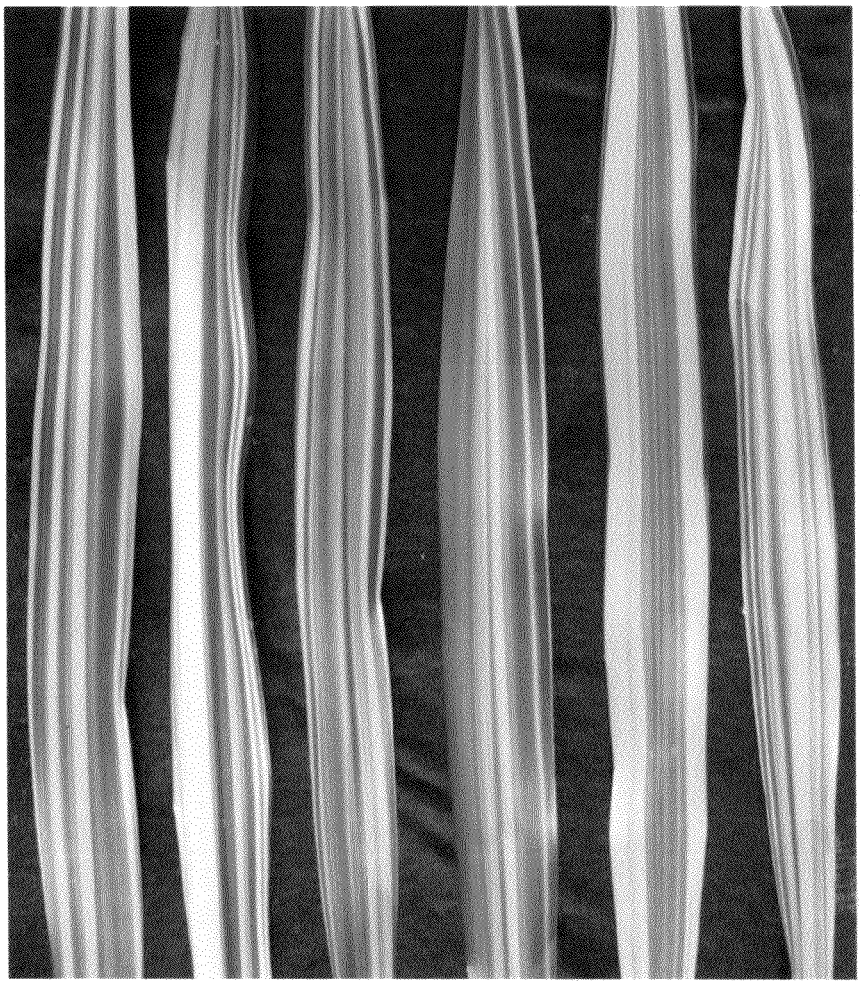

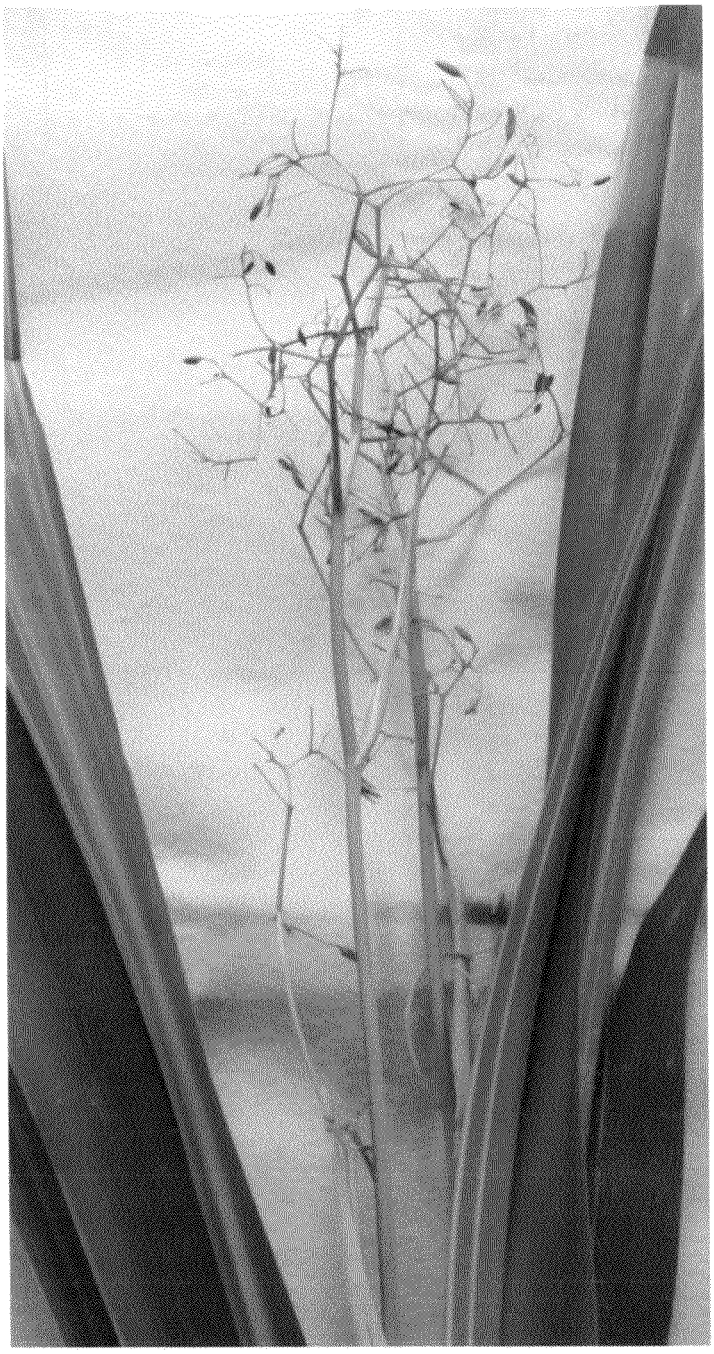

* * * * *